United States Patent
Fort et al.

[11] 3,941,798
[45] Mar. 2, 1976

[54] 5-ALKYL-3-(2-HYDROXYLAMINO-4-CHLOROPHENYL)-1,3,4-OXADIAZOLIN-2-ONE COMPOUNDS

[75] Inventors: Jean-Francois Fort, Paris; Raymond Giraudon, Le Parc de Lesigny, both of France

[73] Assignee: Rhone Poulenc S.A., Paris, France

[22] Filed: Apr. 10, 1975

[21] Appl. No.: 566,971

Related U.S. Application Data
[62] Division of Ser. No. 453,055, March 20, 1974.

[30] Foreign Application Priority Data
Mar. 22, 1973 France............................ 73.10291

[52] U.S. Cl......................... 260/307 A; 260/562 H
[51] Int. Cl.²......................................... C07D 271/10
[58] Field of Search............................... 260/307 A

[56] References Cited
UNITED STATES PATENTS
3,741,977  6/1973  Boesch........................... 260/307 A

*Primary Examiner*—Raymond V. Rush
*Attorney, Agent, or Firm*—Stevens, Davis, Miller & Mosher

[57] ABSTRACT
Oxadiazoline derivatives of the formula:

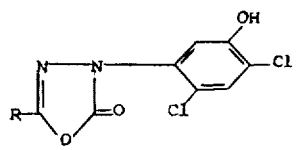

wherein R is alkyl of 1 through 4 carbon atoms, which are useful as intermediates in the synthesis of oxadiazoline derivatives of the formula:

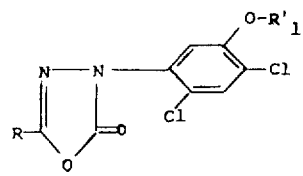

wherein R is as defined above and $R_1$ is alkyl of 1 through 4 carbon atoms, possessing useful herbicidal properties, are prepared by a process which comprises reducing the nitro group in a 5-alkyl-3-(2-nitro-4-chlorophenyl)-1,3,4-oxadiazolin of the formula:

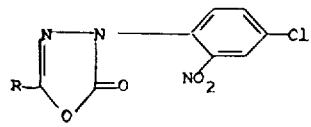

wherein R is as defined above to a hydroxylamino group, subjecting the resulting 5-alkyl-3-(2-hydroxylamino-4-chlorophenyl)-1,3,4-oxadiazolin-2-one to the Bamberger rearrangement, and converting the amine group in the resulting 5-alkyl-3-(2-amino-4-chloro-5-hydroxyphenyl)-1,3,4-oxadiazolin-2-one to a chlorine atom. The 5-alkyl-3-(2-hydroxylamino-4-chlorophenyl)-1,3,4-oxadiazolin-2-one intermediates are compounds.

1 Claim, No Drawings

5-ALKYL-3-(2-HYDROXYLAMINO-4-CHLOROPHENYL)-1,3,4-OXADIAZOLIN-2-ONE COMPOUNDS

This is a division, of application Ser. No. 453,055, filed Mar. 20, 1974.

This invention relates to a new process for the preparation of oxadiazoline derivatives of the general formula:

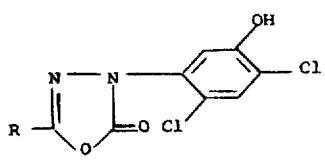

I wherein R represents a straight- or branched-chain alkyl radical containing 1 to 4 carbon atoms.

The compounds of general formula I are useful as intermediates in the synthesis of oxadiazoline derivatives of the general formula:

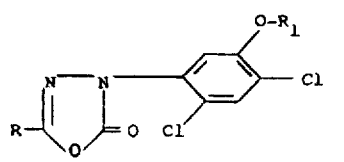

II wherein R is as hereinbefore defined and $R_1$ represents a straight-or branched-chain alkyl radical containing 1 to 4 carbon atoms or an alkynyl radical containing 3 or 4 carbon atoms.

The derivatives of general formula II can be prepared by reacting an alkyl or alkynyl halide of the general formula:

$R_1 - X$   III wherein $R_1$ is as hereinbefore defined and X represents a halogen (preferably bromine or chlorine) atom, with an oxadiazoline derivative of general formula I wherein R is as hereinbefore defined. The reaction is generally carried out in an inert organic solvent, such as acetonitrile, at a temperature between 50°C. and the boiling point of the reaction mixture, and optionally in the presence of an alkaline condensation agent such as potassium carbonate.

The oxadiazoline derivatives of general formula II possess useful herbicidal properties which are described in, for example, the specifications of British Patents Nos. 1,063,799 and 1,345,313, granted to Rhone-Poulenc S.A. on applications filed Dec. 11, 1964 and May 31, 1972 respectively.

The oxadiazoline derivatives of general formula II wherein $R_1$ represents a straight- or barnched-chain alkyl radical containing 1 to 4 carbon atoms may also be prepared by application of the process described in the specifications of British Patents Nos. 1,063,799 and 1,110,500 (granted to Rhone-Poulenc S.A. on an application filed Oct. 27, 1966), by reaction of phosgene with a hydrazide of the general formula:

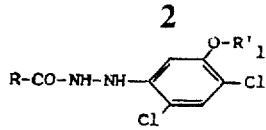

IV wherein R is as hereinbefore defined and $R'_1$ represents a straight- or branched-chain alkyl radical containing 1 to 4 carbon atoms.

The oxadiazoline derivatives of general formula II wherein $R_1$ represents a straight- or branched-chain alkyl radical containing 1 to 4 carbon atoms may, in addition, also be prepared by application of the process described in the specification of British Patent No. 1,286,067 (granted to Rhone-Poulenc S.A. on an application filed Aug. 5, 1970), the process involving the reaction of a halogenonitrobenzene of the general formula:

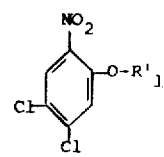

V wherein $R'_1$ is as hereinbefore defined, with an alkali metal salt, optionally prepared in situ, of an oxadiazoline derivative of the general formula:

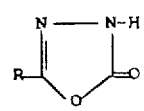

VI wherein R is as hereinbefore defined, followed by reduction of the nitro radical to an amino radical and then replacement of the amino group by a chlorine atom via the diazonium salt.

In British Patent Specification No. 1,345,313 there are described processes for the preparation of oxadiazoline derivatives of general formula II wherein $R_1$ represents an alkynyl radical containing 3 or 4 carbon atoms, the processes involving: (1) reaction of phosgene with a hydrazide of the general formula:

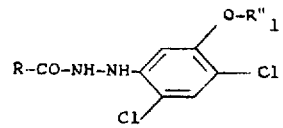

VII wherein R is as hereinbefore defined and $R''_1$ represents an alkynyl radical containing 3 or 4 carbon atoms, or (2) reaction of an alkynyl halide of the general formula:

$R''_1 - X$   VIII wherein $R''_1$ is as hereinbefore defined and X represents a halogen (preferably chlorine) atom, with an oxadiazoline derivative of general formula I, which can be produced either by reacting phosgene with the corresponding hydrazide of the general formula:

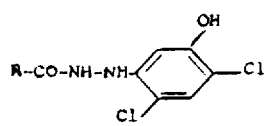

wherein R is as hereinbefore defined, or from an oxadiazoline derivative of general formula II, wherein R is as hereinbefore defined and $R_1$ represents a straight- or branched-chain alkyl radical containing 1 to 4 carbon atoms, by methods known per se for the conversion of an alkoxy group to a hydroxy radical without affecting the rest of the molecule.

It has now been found, and it is this which forms the subject of the present invention, that the oxadiazoline derivatives of general formula I can be prepared easily by the process depicted schematically below:

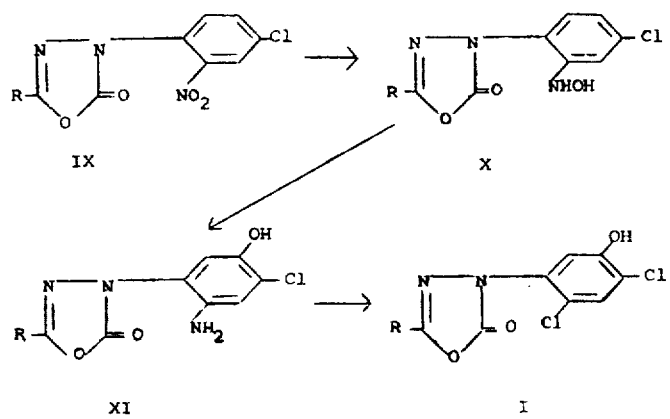

The compounds of general formula IX can be produced by reacting 2,5-dichloro-nitrobenzene with an alkali metal salt of an oxadiazoline of general formula VI in accordance with the method described in the specification of British Patent No. 1,286,067.

The nitro compounds of general formula IX can be converted to the compounds of general formula X by reducing the nitro group to a hydroxylamino group by methods known per se and which do not affect the rest of the molecule. The reduction is preferably carried out by means of hydrogen in the presence of a catalyst, for example palladium on charcoal, at ambient temperature, for example 15°–25°C., and at atmospheric pressure.

The conversion of the hydroxylamine derivatives of general formula X to the aminophenols of general formula XI can be carried out under the general conditions for the Bamberger rearrangement [Chem. Ber., 27, 1347 and 1548 (1894)]. The hydroxylamine derivative of general formula X is preferably treated with a strong inorganic acid, for example sulphuric acid, at a temperature below 25°C.

The conversion of the aminophenols of general formula XI to oxadiazoline derivatives of general formula I can be carried out by methods known per se for the conversion of an amino group to a chlorine atom without affecting the rest of the molecule. The conversion is generally carried out via a corresponding diazonium salt as an intermediate.

The conversion of nitro compounds of general formula IX to the aminophenols of general formula XI can also be carried out directly by working under the conditions which are described in the specification of U.S. Pat. No. 3,535,382 (granted to B. B. Brown and F. A. E. Schilling on Oct. 20, 1970) or in the specification of British Pat. No. 1,229,707 (granted to Rhone-Poulenc S.A. on an application filed Jan. 29, 1969). The conversion may be effected by hydrogenating a heated mixture containing the nitro compound of general formula IX, aqueous sulphuric acid, suspended hydrogenation catalyst and a surfactant prepared by the condensation of an alkylphenol, wherein the alkyl group contains from 8 to 18 carbon atoms, and glycidol. The conversion may also be effected by hydrogenating the nitro compound of general formula IX in the presence of a catalyst based on platinum, in an aqueous solution of sulphuric or phosphoric acid, under a partial pressure of hydrogen exceeding one atmosphere, the nitro compound being injected continuously into the reaction medium.

The oxadiazoline derivatives of general formula I obtained by the process of the present invention may be purified by physical methods such as crystallisation or chromatography.

The hydroxylamine derivatives of general formula X, wherein R is as hereinbefore defined, are new compounds and as such they and the hereinbefore described process for their preparation constitute features of the present invention.

According to a further feature of the present invention oxadiazoline derivatives of the general formula:

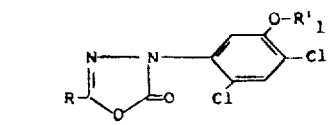   XII (wherein R and $R'_1$ are as hereinbefore defined) are prepared by the process which comprises the reaction of an alkyl halide of the general formula:

$R'_1 - X$   XIII (wherein $R'_1$ and X are as hereinbefore defined) with an oxadiazoline derivative of general formula I.

In this specification the term "methods known per se" means methods heretofore used or described in the chemical literature.

The following Examples illustrate the present invention.

EXAMPLE 1

A solution of 5-(t-butyl)-3-(2-nitro-4-chlorophenyl)-1,3,4-oxadiazolin-2-one (100 g.) in ethyl acetate (800 cc.) containing 3% w/w palladium on charcoal (1.5 g.) is hydrogenated at atmospheric pressure and at approximately 20°C. After the absorption of hydrogen (16 litres) over the course of approximately 4 hours, the hydrogenation is stopped. The catalyst is filtered off and, after cooling the solution, the crystals obtained are filtered off. The filtrate is concentrated and the crystals obtained are filtered off. After recrystallisation of the crystals from acetonitrile, 5-(t-butyl)-3-(2-hydroxylamino-4-chlorophenyl)-1,3,4-oxadiazolin-2-one (38.1 g.) which melts at 195°–196°C., is obtained.

5-(t-Butyl)-3-(2-hydroxylamino-4-chlorophenyl)-1,3,4-oxadiazolin-2-one (22.7 g.) is added in small portions, and whilst keeping the temperature of the reaction mixture between 13° and 21°C., to concentrated sulphuric acid (d = 1.83; 227 cc.). The mixture is stirred at the same temperature for a further 20 minutes. The orange homogeneous solution is poured onto ice (400 g.). The precipitate which appears is filtered off and is then taken up in an aqueous solution of potassium bicarbonate; the suspension obtained is extracted with methylene chloride (200 cc.); after drying the extract and removing the organic solvent under reduced pressure, a product (21.8 g.), which melts at 131°C., is obtained. After recrystallisation from carbon tetrachloride (650 cc.), 5-(t-butyl)-3-(2-amino-4-chloro-5-hydroxyphenyl)-1,3,4-oxadiazolin-2-one (15.5 g.), which melts at 131°–132 C., is obtained.

A solution of 5-(t-butyl)-3-(2-amino-4-chloro-5-hydroxyphenyl)-1,3,4-oxadiazolin-2-one (14.5 g.) in concentrated sulphuric acid (d = 1.83; 72.5 cc.) is diluted, whilst cooling, with water (133 cc.). A solution of sodium nitrite (3.6 g.) in water (14.5 cc.) is then added, with stirring, to the suspension obtained, whilst keeping the temperature of the reaction mixture between 5° and 7°C. After the end of the addition, the diazonium sulphate which precipitates is filtered off and then added to a solution of cuprous chloride (6.5 g.) in concentrated hydrochloric acid (32.5 cc.). The mixture is kept at about 40°C. until the evolution of gas has ceased. After cooling the precipitate is filtered off and washed with N hydrochloric acid (200 cc.) and then with water (6 × 100 cc.). The precipitate is taken up in methylene chloride (150 cc.). After drying the solution and removing the solvent under reduced pressure, a product (13.65 g.), which melts at 126°–129°C., is obtained. After recrystallisation from cyclohexane ( 400 cc.), 5-(t-butyl)-3-(2,4-dichloro-5-hydroxyphenyl)-1,3,4-oxadiazolin-2-one (11.2 g.), which melts at 132°C., is obtained.

5-(t-Butyl)-3-(2-nitro-4-chlorophenyl)-1,3,4-oxadiazolin-2-one, which melts at 79°C., can be produced by condensing 2,5-dichloro-nitrobenzene (382 g.) with 5-(t-butyl)-1,3,4-oxadiazolin-2-one (302 g.) in accordance with the process which is described in the specification of British Patent No. 1,286,067.

EXAMPLE 2

Anhydrous potassium carbonate (468 g.) and sodium iodide (25.4 g.) are added to a solution of 5-(t-butyl)-3-(2,4-dichloro-5-hydroxyphenyl)-1,3,4-oxadiazoline-2-one (1.025 g.) in acetonitrile (5.125 litres). The mixture is heated at about 70°C. Isopropyl bromide (541 g.) is added to this solution and the reaction mixture is heated under reflux, with stirring, for 16 hours. After cooling and filtering off the inorganic salts, which precipitate, the solution is concentrated under reduced pressure. The residue which has crystallised is taken up in methylene chloride (2.33 litres) and the solution obtained is washed successively with water, a 0.5% aqueous solution of sodium hydroxide, and water. After drying the solution and removing the solvent under reduced pressure, a product (1,149 g.), which melts at 88°–89°C., is obtained. On recrystallisation from ethanol (1.149 litres), 5-(t-butyl)-3-(2,4-dichloro-5-isopropoxyphenyl)-1,3,4-oxadiazolin-2-one (1.012 g.), which melts at 89°C., is obtained.

EXAMPLE 3

A solution of 5-isopropyl-3-(2-nitro-4-chlorophenyl)-1,3,4-oxadiazolin-2-one (16 g.) in ethyl acetate (130 cc.) containing 3% w/w palladium on charcoal (1 g.) is hydrogenated at atmospheric pressure and at approximately 20°C. After the absorption of hydrogen (1.9 litres) (70% of the theoretical amount), the reaction is stopped and the reaction mixture is filtered. The filtrate is concentrated under reduced pressure and the residue taken up in benzene (50 cc.); the crystals obtained are filtered off and washed with benzene (15 cc.). 5-Isopropyl-3-(2-hydroxylamino-4-chlorophenyl)-1,3,4-oxadiazolin-2-one (7.2 g.), which melts at 138°–140°C., is obtained. The benzene filtrate is recycled and is subjected to an operation identical to that described above. 5-Isopropyl-3-(2-hydroxylamino-4-chlorophenyl)-1,3,4-oxadiazolin-2-one (2.9 g.), which melts at 138°–140°C., is obtained.

5-Isopropyl-3-(2-hydroxylamino-4-chlorophenyl)-1,3,4-oxadiazolin-2-one (13 g.) is added, in small portions and whilst keeping the temperature of the reaction mixture between 12° and 16°C., to concentrated sulphuric acid (d = 1.83; 130 cc.). The mixture is stirred at the same temperature for 30 minutes. The brownish homogeneous solution is poured onto ice (240 g.). The precipitate obtained is filtered off, then taken up in an aqueous solution of potassium bicarbonate and extracted with ethyl acetate (100 cc.). After drying the ethyl acetate solution and removing the organic solvent under reduced pressure, 5-isopropyl-3-(2-amino-4-chloro-5-hydroxyphenyl)-1,3,4-oxadiazolin-2-one (10.8 g.), which melts at 129°C., is obtained.

A 2N solution of hydrogen chloride in acetone (10 cc.) is added to a solution of 5-isopropyl-3-(2-amino-4-chloro-5-hydroxyphenyl)-1,3,4-oxadiazolin-2-one (5 g.) in acetone (50 cc.); the precipitate thus obtained is filtered off and washed three times with acetone (total 30cc.). The hydrochloride obtained is dissolved in hydrochloric acid (d = 1.19; 50 cc.), and then a solution of sodium nitrite (1.35 g.) in water (6 cc.) is added whilst keeping the temperature of the reaction mixture between 5° and 10°C. After stirring for 15 minutes, a solution of cuprous chloride (2.4 g.) in concentrated hydrochloric acid (15 cc.) is added. The reaction mixture is kept between 30° and 40°C. until the evolution of gas has ceased. After cooling, the precipitate which forms is filtered off and washed with N hydrochloric acid (100 cc.) and then three times with water (total 300 cc.). The precipitate is taken up in methylene chloride (80 cc.). After drying the methylene chloride solution and removing the solvent under reduced pressure, a product (4.2 g.), which melts at 122°C., is obtained. After recrystallisation from benzene (20 cc.), 5-isopropyl-3-(2,4-dichloro-5-hydroxyphenyl)-1,3,4-oxadiazolin-2-one (3.5 g.), which melts at 126°C., is obtained. 5-Isopropyl-3-(2-nitro-4-chlorophenyl)-1,3,4-oxadiazolin-2-one, which melts at 68°C., can be produced by condensing 2,5-dichloro-nitrobenzene (115.5 g.) with 5-isopropyl-1,3,4-oxadiazolin-2-one (100 g.), in accordance with the process which is described in British Patent Specification No. 1,286,067.

EXAMPLE 4

Potassium carbonate (13.8 g.) is added to a solution of 5-isopropyl-3-(2,4-dichloro-5-hydroxyphenyl)-1,3,4-oxadiazolin-2-one (28.9 g.) in acetonitrile (150 cc.), and the mixture is heated at about 70°C. Isopropyl bromide (14.8 g.) is added and the mixture is heated under reflux for 13 hours. After cooling the mixture and filtering off the inorganic salts, the solution is concentrated under reduced pressure. The residue is taken up in methylene chloride (150 cc.), and the solution obtained is washed successively with water, a 0.5% aqueous solution of sodium hydroxide, and water. After drying the methylene chloride solution and removing the organic solvent under reduced pressure, a product (33 g.), which melts at 90°C., is obtained. On recrystallisation from cyclohexane (100 cc.), 5-isopropyl-3-(2,4-dichloro-5-isopropoxyphenyl)-1,3,4-oxadiazolin-2-one (26.5 g.), which melts at 96°–98°C., is obtained.

We claim:

1. A hydroxylamine compound of the formula:

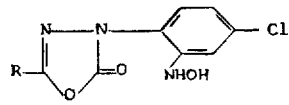

wherein R is alkyl of 1 through 4 carbon atoms.

* * * * *